United States Patent
Kroll (12)

(10) Patent No.: US 6,751,503 B1
(45) Date of Patent: Jun. 15, 2004

(54) METHODS AND SYSTEMS FOR TREATING PATIENTS WITH CONGESTIVE HEART FAILURE (CHF)

(75) Inventor: Mark W. Kroll, Simi Valley, CA (US)

(73) Assignee: Pacesetter, Inc., Sylmar, CA (US)

( * ) Notice: Subject to any disclaimer, the term of this patent is extended or adjusted under 35 U.S.C. 154(b) by 355 days.

(21) Appl. No.: 09/999,408

(22) Filed: Nov. 1, 2001

(51) Int. Cl.[7] .............................................. A61N 1/365
(52) U.S. Cl. ...................................................... 607/18
(58) Field of Search ............................. 607/9, 17, 18, 607/25

(56) References Cited

U.S. PATENT DOCUMENTS

| | | | |
|---|---|---|---|
| 5,334,222 A | * | 8/1994 | Salo et al. ..................... 607/17 |
| 5,554,177 A | * | 9/1996 | Kieval et al. .................. 607/17 |
| 5,700,283 A | | 12/1997 | Salo .............................. 607/17 |
| 5,800,471 A | | 9/1998 | Baumann ...................... 607/25 |
| 5,836,987 A | * | 11/1998 | Baumann et al. ............. 607/17 |
| 5,876,353 A | * | 3/1999 | Riff .............................. 600/547 |
| 5,891,176 A | | 4/1999 | Bornzin ........................ 607/18 |
| 6,104,949 A | * | 8/2000 | Pitts Crick et al. .......... 600/547 |
| 6,223,082 B1 | | 4/2001 | Bakels et al. ................. 607/17 |

\* cited by examiner

*Primary Examiner*—Carl Layno

(57) ABSTRACT

Various embodiments provide techniques and systems that can ensure that patients with congestive heart failure receive pacing therapy that optimizes their hemodynamic performance in view of various variables that pertain to the patient. Exemplary variables can include, without limitation, the time of day, patient posture and activity level.

42 Claims, 7 Drawing Sheets

US 6,751,503 B1

METHODS AND SYSTEMS FOR TREATING PATIENTS WITH CONGESTIVE HEART FAILURE (CHF)

TECHNICAL FIELD

The present invention generally relates to implantable stimulation devices and methods and systems for treating patients with congestive heart failure (CHF).

BACKGROUND

Congestive heart failure (CHF) is defined generally as the inability of the heart to deliver enough blood to the peripheral tissues to meet metabolic demands. Frequently, CHF is manifested by left heart dysfunction, but it can have a variety of sources. For example, CHF patients may have any one of several different conduction defects. The natural electrical activation system through the heart involves sequential events starting with the sino-atrial (SA) node, and continuing through the atrial conduction pathways of Bachmann's bundle and internodal tracts at the atrial level, followed by the atrio-ventricular (AV) node, Common Bundle of His, right and left bundle branches, and final distribution to the distal myocardial terminals via the Purkinje fiber network. A common type of intra-atrial conduction defect is known as intra-atrial block—a condition where the atrial activation is delayed in getting from the right atrium to the left atrium. In left bundle branch block and right bundle branch block, the activation signals are not conducted in a normal fashion along the right or left bundle branches respectively. Thus, in a patient with bundle branch block, the activation of the ventricle is slowed, and the QRS is seen to widen due to the increased time for the activation to traverse the conduction path.

CHF manifested by such conduction defects and/or other cardiomyopathies are the object of considerable research into treatments for improving cardiac output. In a healthy heart, cardiac output is typically not a problem. In patients with CHF, cardiac output is typically a problem. Because an unhealthy heart does not function properly insofar as important timing issues are concerned (e.g. A-V timing and V-V timing), cardiac output can be adversely affected. Hence, there is a continuing need to address timing issues in CHF patients. More specifically, there is a continuing need to provide improved cardiac output for CHF patients.

Accordingly, this invention arose out of concerns associated with providing improved methods and systems for determining desirable or optimal timing parameters for pacing CHF patients.

SUMMARY

Various embodiments provide techniques and systems that can ensure that patients with congestive heart failure receive pacing therapy that optimizes their hemodynamic performance in view of various variables that pertain to the patient. Exemplary variables can include, without limitation, the time of day, patient posture and activity level.

BRIEF DESCRIPTION OF THE DRAWINGS

The following description is of the best mode presently contemplated for practicing the invention. This description is not to be taken in a limiting sense but is made merely for the purpose of describing the general principles of the invention. The scope of the invention should be ascertained with reference to the issued claims.

DETAILED DESCRIPTION

Figure 1:
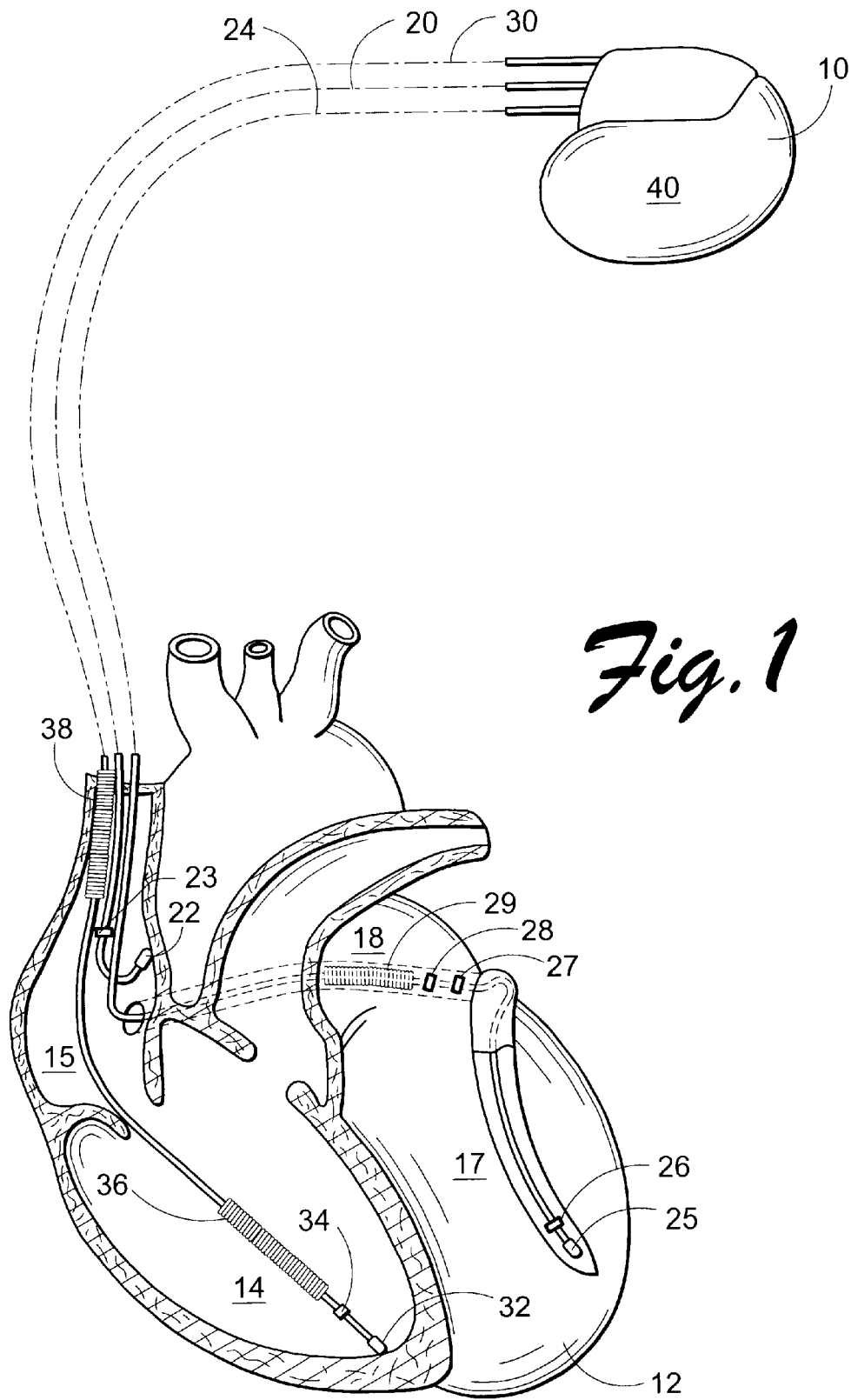
FIG. 1 is a simplified diagram illustrating an implantable stimulation device in electrical communication with at least three leads implanted into a patient's heart for delivering multi-chamber stimulation and shock therapy.

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

Overview

There are typically two important timing considerations that pertain to pacing a patient with congestive heart failure (CHF). The first is the timing between the atria and the ventricles (known as the "A-V timing"), and the second is the timing between the right ventricle and the left ventricle (known as the "V-V timing"). In a healthy heart, there is a fairly consistent relationship that defines the A-V timing and the V-V timing. When a patient has CHF, however, the heart muscle does not function properly and, hence, timing disparities can exist. This leads to problems associated with trying to find desirable or optimal A-V and V-V timing for purposes of pacing CHF patients.

In the embodiments described below, the hemodynamic performance of a CHF patient is monitored by an implanted stimulation device. This can be done by monitoring the patient's cardiac output. A patient's cardiac output can be monitored using any number of known sensors. Such sensors can allow such things as stroke volume and other parameters associated with a patient's cardiac output to be monitored. Multiple different variables associated with the patient are monitored and timing parameters associated with A-V and/or V-V timing (i.e. those timing parameters that optimize the patient's hemodynamic performance) are ascertained in an attempt to optimize the patient's hemodynamic performance for a given set of variables. In the described embodiments, the monitored variables are independent of the patient's heart function. The timing parameters are stored in the stimulation device and, if a patient is determined to subsequently satisfy a given set of variables for which timing parameters exist, the timing parameters are used to pace the patient. If, for a given set of variables, timing parameters do not exist, then the stimulation device is programmed to automatically determine optimal timing parameters and store those parameters in memory for future use. Over time, a patient profile is developed and used to pace the patient in a manner that optimizes their hemodynamic performance for a given set of variables. In this document the term "optimize" is used to describe a patient's hemodynamic performance as provided by one or more "optimized" timing parameters that are used to pace the patient. The term "optimize" is used in a relative sense to include, not only factually optimal hemodynamic performance, but improved hemodynamic performance that is improved over hemodynamic performance that would otherwise exist in the absence of the inventive techniques described herein.

Exemplary Stimulation Device

The following description sets forth but one exemplary stimulation device that is capable of being used in connection with the various embodiments that are described below. It is to be appreciated and understood that other stimulation devices, including those that are not necessarily implantable, can be used and that the description below is given, in its specific context, to assist the reader in understanding, with more clarity, the inventive embodiments described herein.

FIG. 1 illustrates a stimulation device 10 in electrical communication with a patient's heart 12 suitable for delivering multi-chamber stimulation and shock therapy. The portions of the heart 10 illustrated include the right ventricle 14, the right atrium 15, the left ventricle 17, and the left atrium 18. As used herein, the left-side of the heart is meant to denote the portions of the heart encompassing the left ventricle 17 and the left atrium 18 and those portions of the coronary sinus, great cardiac vein, and its associated tributaries, which are adjacent the left atrium and left ventricle.

To sense atrial cardiac signals and to provide right atrial chamber stimulation therapy, the stimulation device 10 is coupled to an implantable right atrial lead 20 having at least an atrial tip electrode 22, and preferably a right atrial ring electrode 23, which typically is implanted in the patient's right atrial appendage.

To sense left atrial and ventricular cardiac signals and to provide left-chamber pacing therapy, the stimulation device 10 is coupled to a "coronary sinus" lead 24 designed for placement in the "coronary sinus region" via the coronary sinus os so as to place one or more distal electrodes adjacent to the left ventricle and one or more proximal electrodes adjacent to the left atrium 18. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver: left ventricular pacing therapy using, for example, a left ventricular tip electrode 25 and a left ventricular ring electrode 26; left atrial pacing therapy using, for example, a first and second left atrial ring electrode, 27 and 28; and shocking therapy using at least a left atrial coil electrode 29.

The stimulation device 10 is also shown in electrical communication with the patient's heart 12 by way of an implantable right ventricular lead 30 having a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle 14.

Figure 2:
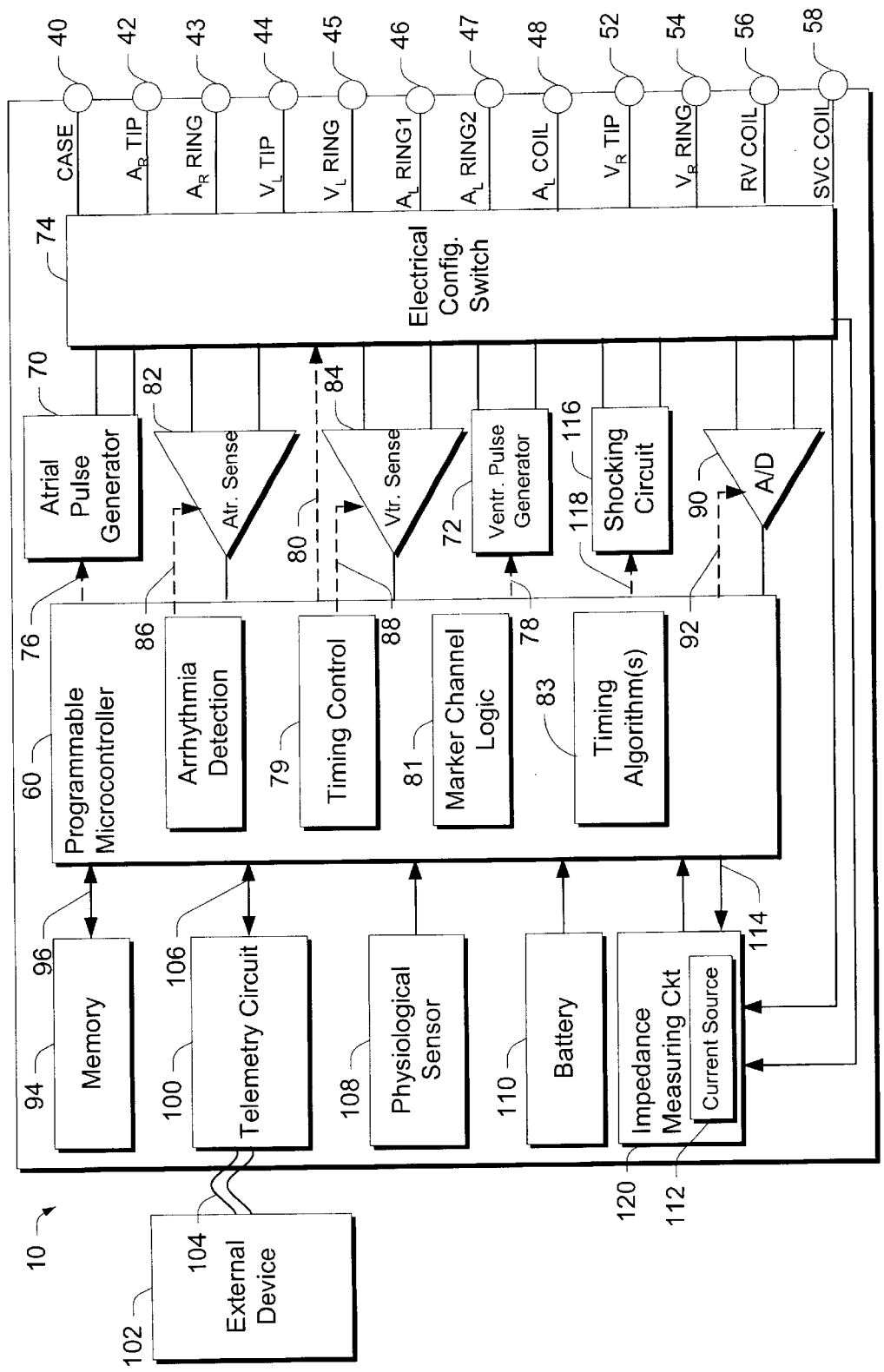
FIG. 2 is a functional block diagram of a multi-chamber implantable stimulation device illustrating exemplary basic elements of a stimulation device which can provide cardioversion, defibrillation and/or pacing stimulation in up to four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and/or pacing stimulation. In addition, it will be appreciated and understood that various processing steps about to be described can be implemented in the form of software instructions that are resident on a computer-readable media that is located on the stimulation device. Accordingly, aspects of the invention described herein extend to all forms of computer-readable media, whether on the stimulation device (or monitoring device) or not, when such media contains instructions that, when executed by one or more processors, implement the methods described herein.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 29, 36, or 38, for shocking purposes.

The housing 40 further includes a connector (not shown) having a plurality of terminals, 42, 43, 44, 45, 46, 47, 48, 52, 54, 56, and 58 (shown schematically and, for convenience, the names of the electrodes to which they are connected are shown next to the terminals). While it is recognized that current devices are limited to the number of terminals due to International Standards, one of skill in the art could readily eliminate some of the terminals/electrodes to fit in the existing device configurations and permit programmability to select which terminals connect to which electrodes. However, in the near future, the standards may change to permit multi-polar in-line connectors, and multiple feedthroughs connectors could readily be manufactured to accommodate the configuration shown in FIG. 2.

As such, to achieve right atrial sensing and pacing, the connector includes at least a right atrial tip terminal 42 and a right atrial ring terminal 43, adapted for connection to the atrial tip electrode and ring electrodes 22 and 23, respectively.

To achieve left chamber sensing, pacing and/or shocking, the connector includes at least a left ventricular tip terminal 44, a left ventricular ring electrode 45, a first left atrial ring terminal 46, a second left atrial ring terminal 47, and a left atrial shocking terminal 48, which are adapted for connection to the left ventricular tip electrode 25, left ventricular ring 26, the first left atrial tip electrode 27, the second left atrial ring electrode 28, and the left atrial coil electrode 29, respectively.

To support right chamber sensing, pacing and/or shocking, the connector further includes a right ventricular tip terminal 52, a right ventricular ring terminal 54, a right ventricular (RV) shocking terminal 56, and an SVC shocking terminal 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller or microprocessor 60 that controls the various modes of stimulation therapy. As is well known in the art, the microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. The details of the design and operation of the microcontroller 60 are not critical to the present invention. Rather, any suitable microcontroller 60 may be used that carries out the functions described herein. The use of microprocessor-based control circuits for performing timing and data analysis functions are well known in the art.

As shown in FIG. 2, an atrial pulse generator 70 and a ventricular pulse generator 72 generate pacing stimulation pulses for delivery by the right atrial lead 20, the right ventricular lead 30, and/or the coronary sinus lead 24 via a switch bank 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interconduction (A-A) delay, or ventricular interconduction (V-V) delay, etc.), as well as to keep track of the timing of refractory periods, PVARP intervals, noise detection windows, evoked response windows, alert intervals, marker channel timing (via marker channel logic 81), etc., which is well known in the art.

In one embodiment, the microcontroller can be programmed with one or timing algorithms 83. The timing algorithm(s) can operate to enable various timing parameters to be adjusted to determine optimal hemodynamic performance of a patient with congestive heart failure (CHF).

The switch bank 74 includes a plurality of switches for connecting the desired electrodes to the appropriate I/O circuits, thereby providing complete electrode programmability. Accordingly, the switch bank 74, in response to a control signal 80 from the microcontroller 60, determines the polarity of the stimulation pulses (e.g. unipolar, bipolar, combipolar, etc.) and various shocking vectors by selectively closing the appropriate combination of switches (not shown) as is known in the art.

Atrial sensing circuits 82 and ventricular sensing circuits 84 may also be selectively coupled to the right atrial lead 20, coronary sinus lead 24, and the right ventricular lead 30, through the switch bank 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch bank 74 determines the "sensing polarity" of the cardiac signal by selectively closing the appropriate switches. In this way, the clinician may program the sensing polarity independent of the stimulation polarity.

The atrial sensing circuit 82 or the ventricular sensing circuit 84 preferably employ one or more low power, precision amplifiers with programmable gain and/or automatic gain control, bandpass filtering, and a threshold detection circuit, to selectively sense the cardiac signal of interest. The automatic gain control enables the stimulation device 10 to deal effectively with the difficult problem of sensing the low amplitude signal characteristics of atrial or ventricular fibrillation. The outputs of the atrial and ventricular sensing circuits, 82 and 84, are connected to the microcontroller 60 for triggering or inhibiting the atrial and ventricular pulse generators, 70 and 72, respectively, in a demand fashion, in response to the absence or presence of cardiac activity, respectively, in the appropriate chambers of the heart.

For arrhythmia detection, the stimulation device 10 utilizes the atrial and ventricular sensing circuits, 82 and 84, to sense cardiac signals for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g. P-waves, R-waves, and depolarization signals associated with fibrillation which are sometimes referred to as "F-waves" or "Fib-waves") are then classified by the microcontroller 60 by comparing them to a predefined rate zone limit (e.g. bradycardia, normal, low rate VT, high rate VT, and fibrillation rate zones) and various other characteristics (e.g. sudden onset, stability, physiologic sensors, and morphology, etc.) in order to determine the type of remedial therapy that is needed (e.g. bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system, analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 can further include one or more physiologic sensors 108. Some physiologic sensors are referred to as a "rate-responsive" sensors because they are typically used to adjust pacing stimulation rate according to the exercise state of the patient. However, physiological sensors 108 may further be used to detect changes in cardiac output, changes in the physiological condition of the heart, patient activity, or diurnal changes in activity (e.g. detecting sleep and wake states). A physiological parameter of the heart, which may be measured to optimize such pacing and to indicate when such pacing may be inhibited or terminated is the stroke volume of the heart. Accordingly, the microcontroller 60 responds by adjusting the various pacing parameters (such as rate, AV Delay, A-A Delay, V-V Delay, etc.) at which the atrial and ventricular pulse generators, 70 and 72, generate stimulation pulses. A common type of rate responsive sensor is an activity sensor, such as an accelerometer or a piezoelectric is crystal, which is mounted within the housing 40 of the stimulation device 10. Other types of physiologic sensors are also known, for example, sensors which sense the oxygen content of blood, respiration rate and/or minute ventilation, pH of blood, ventricular gradient, etc.

The stimulation device 10 additionally includes a power source such as a battery 110 that provides operating power to all the circuits shown in FIG. 2. For the stimulation device 10, which employs shocking therapy, the battery 110 is capable of operating at low current drains for long periods of time, and also be capable of providing high-current pulses (for capacitor charging) when the patient requires a shock pulse. The battery 110 preferably has a predictable discharge characteristic so that elective replacement time can be detected. Accordingly, the stimulation device 10 can employ lithium/silver vanadium oxide batteries.

It can be a primary function of the stimulation device 10 to operate as an implantable cardioverter/defibrillator (ICD) device. That is, it can detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 joules), moderate (0.5–10 joules), or high (11 to 40 joules) energy, as controlled by the microcontroller 60. Such shocking pulses are applied to the patient's heart through at least two shocking electrodes, and as shown in this embodiment, selected from the left atrial coil electrode 29, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the left atrial coil electrode 29 (i.e., using the RV electrode as the common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

As further shown in FIG. 2, the stimulation device 10 can have an impedance measuring circuit 120 including an impedance measuring current source 112 and a voltage measuring circuit 90 (shown in FIG. 2 as an A/D converter), which can be enabled by the microcontroller 60 by a control signal 114 for providing stroke volume measurements of the heart. The current source 112 can provide an alternating or pulsed excitation current. The voltage measuring circuitry 90 may also take the form of, for example, a differential amplifier.

The uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring a respiration parameter (for example, tidal volume, respiration rate, minute ventilation or volume, abnormal or periodic breathing); measuring thoracic impedance for determining shock thresholds and shock timing (corresponding to the diastolic time); detecting when the device has been implanted; measuring a cardiac parameter (such as, stroke volume, wall thickness, left ventricular volume, etc.); and detecting the opening of the valves, etc. In the present embodiment, the impedance measuring circuit is used to monitor left heart disease and provides appropriate stimulation therapy, such as altering rate, AV, A-A, or V-V delays. The impedance measuring circuit 120 can be advantageously coupled to the switch bank 74 so that any desired electrode can be used. Impedance may also be useful in verifying hemodynamic collapse to confirm that ATP has failed and/or VF has begun.

The microcontroller 60 is coupled to the voltage measuring circuit 90 and the current source 112 for receiving a magnitude of the established current and a magnitude of the monitored voltage. The microcontroller 60, operating under program instructions, divides the magnitude of the monitored or measured voltage by the magnitude of the established current to determine an impedance value. Once the impedance signals are determined, they may be delivered to the memory 94 for storage and later retrieved by the microcontroller 60 for therapy adjustment or telemetry transmission. The telemetry circuitry receives the impedance values from the microcontroller 60 and transmits them to the external programmer. The impedance value may then be monitored by the patient's physician to enable the physician to track the patient's condition.

The impedance measuring circuit 120 is advantageously coupled to the switch bank 74 so that any desired electrode may be used. The current source 112 may be programmably configured between a desired pair of electrodes, and the voltage measuring circuit 90 may be programmably configured between the same or preferably a different pair of electrodes.

Exemplary Method

Figure 3:
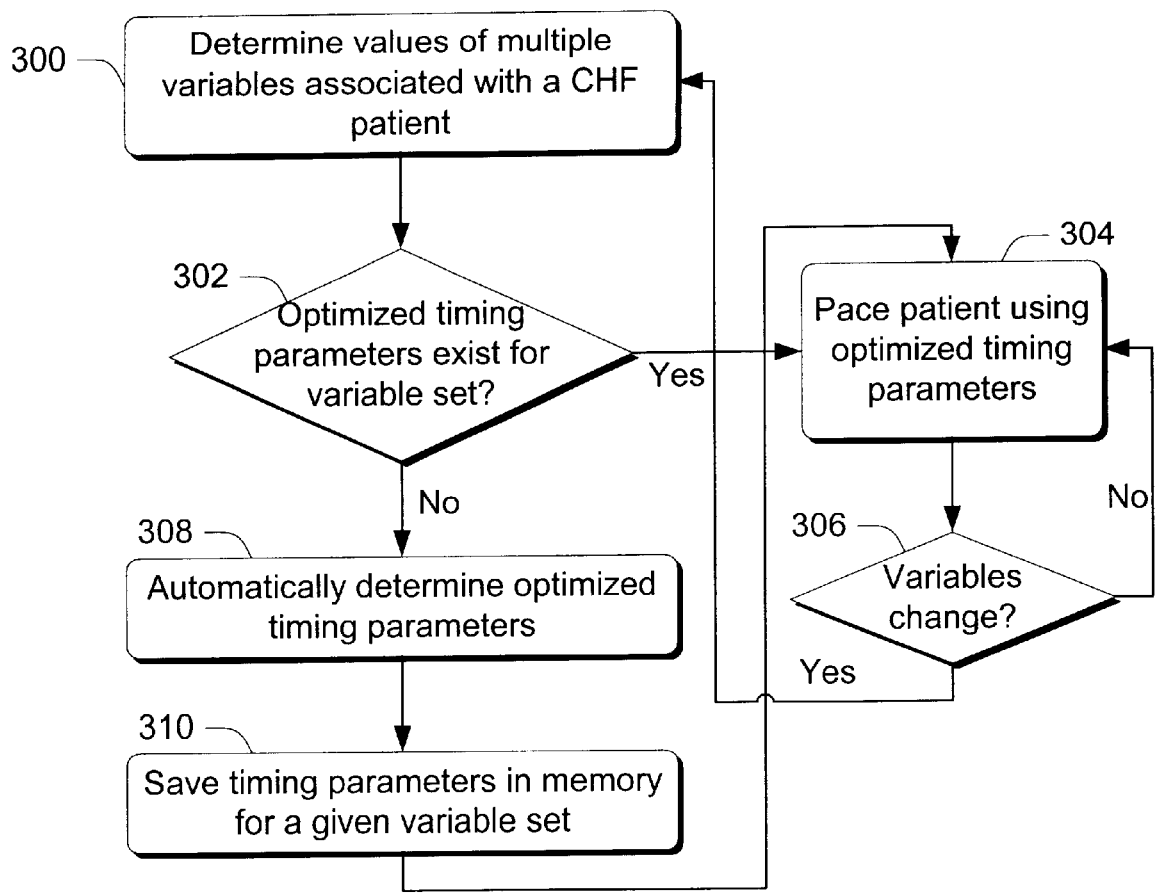
FIG. 3 is a flow diagram that describes steps in a method in accordance with one embodiment.

FIG. 3 is a flow diagram that describes steps in a method in accordance with one embodiment. The method can be implemented in any suitable hardware, software, firmware or combination thereof. In one embodiment, the method can be implemented by a suitably programmed stimulation device.

Step 300 determines values of multiple variables associated with a CHF patient. Exemplary variables can include, without limitation, the time of day, patient's posture, and activity level of the patient. The values of these variables can be determined using known sensors or components that comprise part of the stimulation device. For example, the time of day can be determined by an internal clock. The patient's posture can be determined using known techniques and sensors. For example, one or more accelerometers can be used to determine the patient's posture. The activity level of the patient can be determined using known activity sensors.

Step 300 thus provides a set of variable values. Step 302 determines, for a given variable set, whether optimized timing parameters exist. The optimized timing parameters can comprise those associated with one or both of A-V and V-V timing. The stimulation device can implement this step by checking in memory to determine whether, for a given set of variables, there exists optimized timing parameters. If optimized timing parameters exist for a given set of variables, then step 304 paces the patient using the optimized timing parameters. Step 306 then determines whether any of the variable values change. If not, then the method loops back to step 304 and continues pacing the patient using the timing parameters associated with the given variable set. If, on the other hand, the variable values change, then the method loops back to step 300 and determines the values of the variables. It is to be appreciated and understood that the variables can have ranges that define tolerances within which they can be considered as unchanged.

If step 302 determines that optimized timing parameters do not exist for a given variable set, then step 308 automatically determines optimized timing parameters for the variable set. This step can be implemented in any suitable way, examples of which are given below in the section entitled "Determining Optimized Timing Parameters". Step 310 then saves the timing parameters in memory for a given variable set and step 304 paces the patient using the optimized timing parameters.

Over time, this method can build a patient profile so that for a given set of variables, optimized timing parameters can be selected and automatically used to pace the patient so that the patient's hemodynamic performance is optimized.

Determining Optimized Timing Parameters

Figure 4:
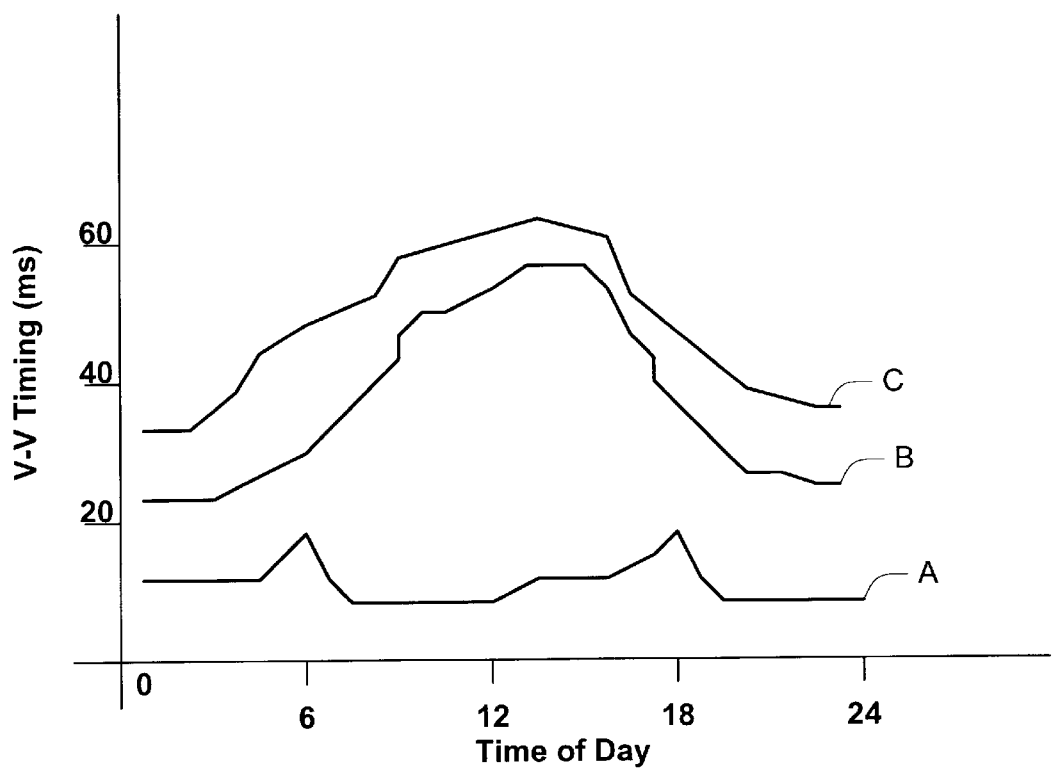
FIG. 4 is a graph that is useful in understanding various inventive embodiments.

Before discussing various ways in which optimized timing parameters can be determined, consider FIG. 4.

FIG. 4 shows an exemplary optimal V-V timing profile for a particular patient. In this example, there are three different profiles designated "A", "B", and "C" as a function of the time of day. Profile A shows a curve that describes the optimal timing for the patient in a supine position through the day. Profile B shows a curve that describes the optimal timing for the patient in an upright position but resting (while, for example, sitting in a chair). Profile C shows a curve that describes the optimal timing for the patient in an upright position while exercising at a maximum exercise rate. Notice that the optimal V-V timing varies as a function of the time of day, patient posture and activity level. By recognizing that timing parameters (such as V-V timing and A-V timing) vary in accordance with these variables, various embodiments can take steps to ensure that a patient with congestive heart failure is paced at a level that is appropriate and optimal for them.

Now, consider the situation in which one wishes to ascertain optimal timing parameters when the patient is in the upright position for all applicable activity levels and times of day. Over time, in accordance with the discussion pertaining to FIG. 3 above, a patient profile can be developed in which, for the possible combinations of times of day and activity levels when the patient is in the upright position, optimal timing parameters are ascertained.

Figure 5:
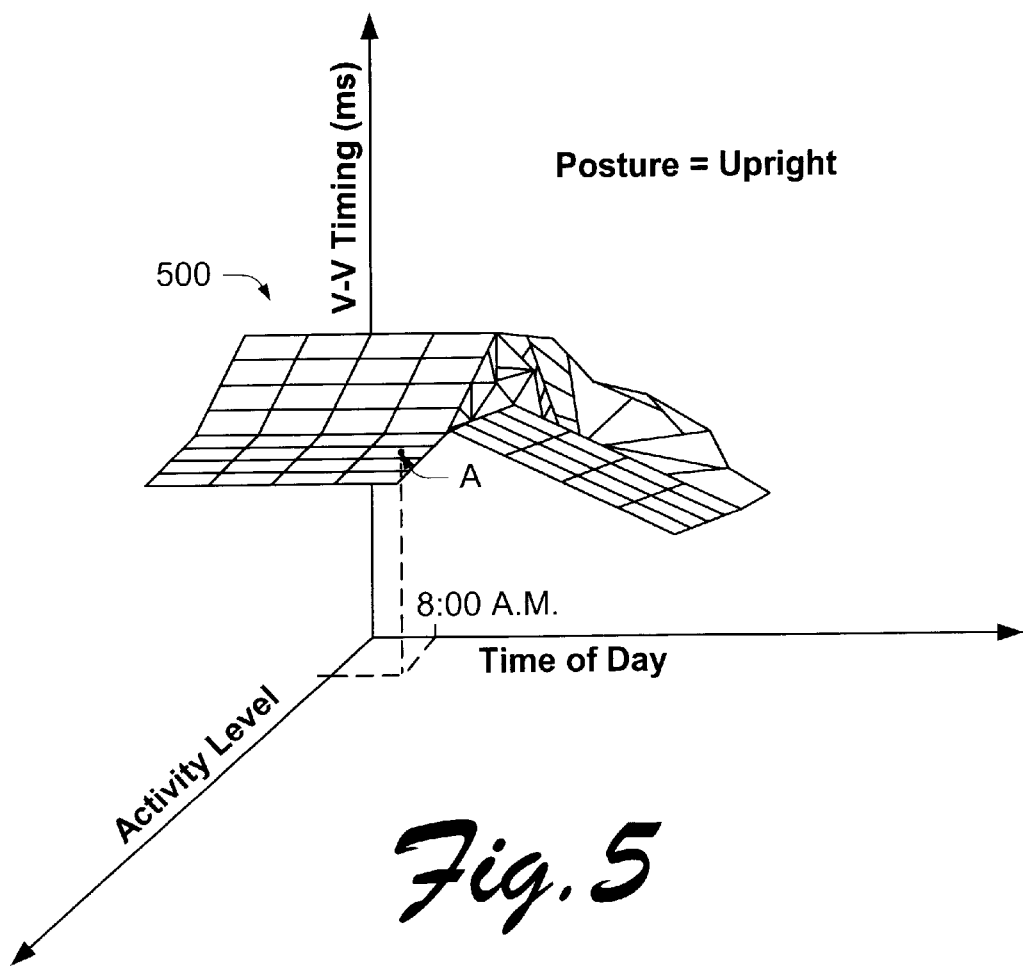
FIG. 5 illustrates a three dimensional surface that can be constructed in accordance with one or more described embodiments.

FIG. 5 shows but one example of how the optimal timing parameters for the upright position can be expressed generally at 500. In this example, a three dimensional plot defines a surface that represents the optimal V-V timing in milliseconds as a function of the time of day and activity level. Thus, when a person is determined to be in the upright position, the stimulation device need only ascertain the time of day and activity level of the patient in order to select the appropriate timing parameters for pacing the patient for V-V timing. Specifically, assume that the stimulation device ascertains that the patient is in the upright position. Assume further that the time of day is determined to be 8:00 A.M and the level of activity is low. As shown in FIG. 5, a point on surface 500 can be found for the corresponding time and activity level (i.e. point A in the figure). This point corresponds to a V-V timing parameter that can then be used to pace the patient. It is to be appreciated that a similar surface can be defined for A-V timing. Additionally, other surfaces can be defined for other patient postures so that for any combination of postures, times of day and activity levels, the appropriate timing parameters for pacing a patient can be ascertained.

Figure 6:
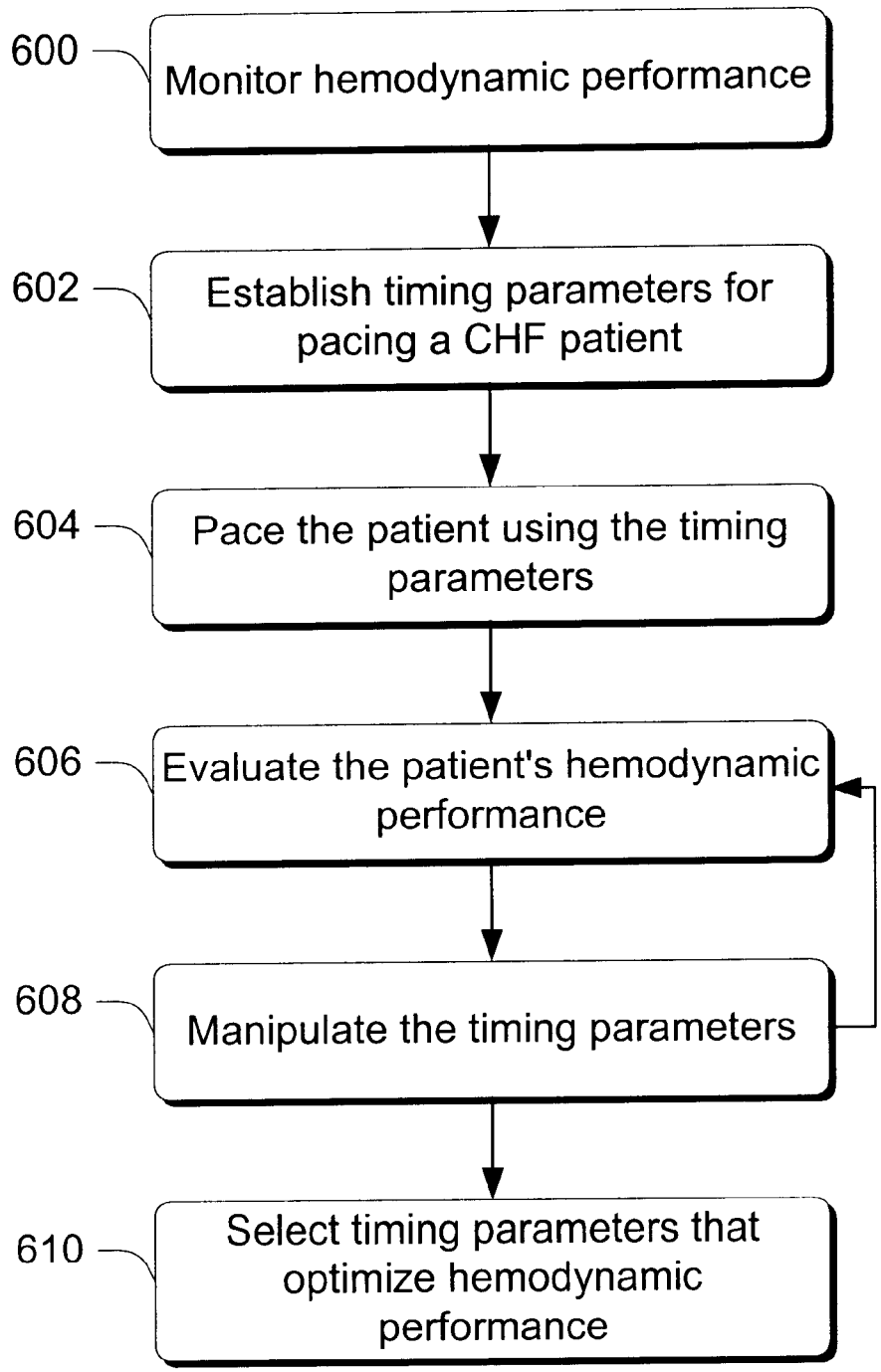
FIG. 6 is a flow diagram that describes steps in a method in accordance with one embodiment.

FIG. 6 is a flow diagram that describes steps in a method in accordance with one embodiment. The method can be implemented in any suitable hardware, software, firmware or combination thereof. In one embodiment, the method can be implemented by a suitably programmed stimulation device. The method about to be described embellishes step 308 in FIG. 3 above.

Step 600 monitors the patient's hemodynamic performance. Monitoring of the hemodynamic performance can take place using any suitable metrics that can be used to monitor hemodynamic performance. Step 602 establishes timing parameters for pacing a CHF patient. This step can be implemented in any suitable manner. For example, the step can be implemented using preprogrammed parameters or by using a set of base line parameters. Step 604 paces the patient using the established timing parameters. Step 606 evaluates the patient's hemodynamic performance in light of the timing parameters and step 608 manipulates the timing parameters. Manipulation of the timing parameters can take place using any suitable manipulation techniques. Specific examples are given below in the section entitled "Manipulation of Timing Parameters". Step 608 desirably loops back to step 606 and continues to evaluate and manipulate the timing parameters for purposes of hemodynamic evaluation. Looping back between steps 608 and 606 can take place any desirable number of times.

Step 610 then selects the timing parameters that optimize the patient's hemodynamic performance. For example, as steps 608 and 606 loop back and forth, hemodynamic performance data can be recorded by the stimulation device. After a number of evaluations have taken place, step 610 can select the timing parameters that are associated with the best hemodynamic performance for that patient. Thus, the method selects the timing parameters that optimize the patient's hemodynamic performance given the universe of acquired hemodynamic performance data.

Manipulation of Timing Parameters

Manipulation of the timing parameters in order to ascertain the timing parameters that optimize the patient's hemodynamic parameters can take place in a number of different ways.

Figure 7:
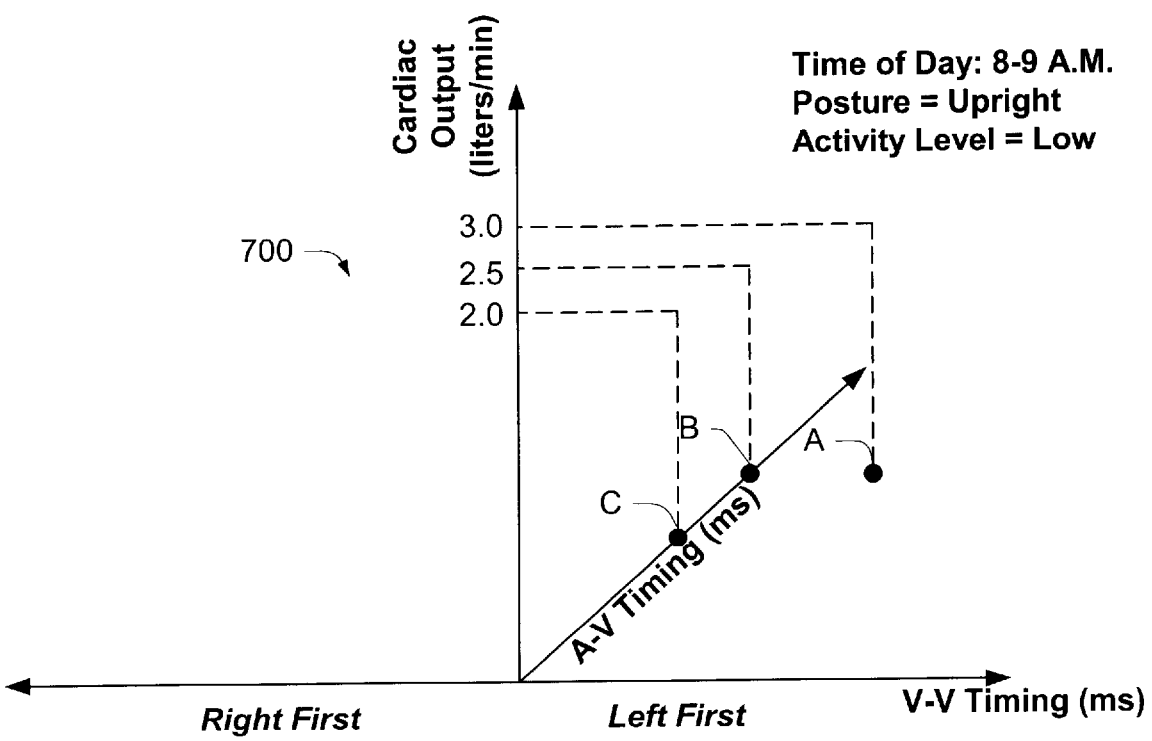
FIG. 7 is a graph that is useful in understanding various inventive embodiments.

In one embodiment, manipulation of the timing parameters can take place through a dithering process in which the timing parameters are manipulated, perhaps randomly, in a trial and error way. As an example, consider FIG. 7.

There, a graph 700 has three axes—a cardiac output axis expressing cardiac output in liters/minute, an A-V timing axis and a V-V timing axis, both of which are expressed in milliseconds. The graph represents data that is taken for the following variable values: time of day=8–9 A.M.; posture= upright; and activity level=low. Assume that the A-V timing is established at 200 ms, and the V-V timing is established at 0 ms, thus corresponding to point B. This means that there is a 200 ms difference in the A-V timing and a 0 ms difference in the V-V timing. At these points in this graph, the cardiac output is ascertained to be equal to 2.5 liters/minute as indicated. Now, assume that the A-V timing is maintained at the previous 200 ms and that the V-V timing is manipulated to equal 30 ms, with the left ventricle being stimulated first, thus corresponding to point A. When the patient's hemodynamic performance is evaluated in terms of their cardiac output, the cardiac output is determined to be about 3.0 liters/minute. Since this is more than the previous cardiac output, the associated timing parameters would be a better choice. Assume now that the timing parameters are manipulated to provide 180 ms A-V timing and 0 ms V-V timing, thus corresponding with point C. At these timing parameters, the cardiac output is observed to be equal to 2.0 liters/minute. Since this cardiac output is less than the cardiac output associated with point A, selection of the parameters associated with point C would not be optimal.

Hence, if these three data points (A, B, and C) were the only three data points for the given patient variables (i.e. time of day=8–9 A.M; posture=upright; and activity level= low), then the parameters associated with point A would be selected and stored as the parameters that optimize hemodynamic performance for the given patient variables. This point is shown on surface 500 (FIG. 5) as the point that represents an optimized V-V timing.

It should be noted, then, that the problem described above is essentially an optimization problem. Accordingly, and as a more preferred alternative to performing a trial and error manipulation of the timing parameters, a number of different optimization methods can be used and will be understood and appreciated by the skilled artisan.

As but a few examples, an optimization method known as the "steepest descent" method can be used. Steepest descent techniques are known and will be appreciated by those of skill in the art. For example, U.S. Pat. No. 5,987,328 discusses, generally, steepest descent techniques. Alternate techniques can be utilized and include, without limitation, the so-called "simplex" method. Simplex techniques are known and are not described in detail here. Additional material on the simplex method of optimization can be found in U.S. Pat. Nos. 5,732,193 and 5,677,857.

Conclusion

In the embodiments described above, techniques and systems can ensure that patients with congestive heart failure receive pacing therapy that optimizes their hemodynamic performance in view of various variables that pertain to the patient. Exemplary variables described in this document include the time of day, patient posture and activity level. It is to be appreciated and understood that other variables could be utilized without departing from the spirit of the claimed subject matter.

Although the invention has been described in language specific to structural features and/or methodological steps, it is to be understood that the invention defined in the appended claims is not necessarily limited to the specific features or steps described. Rather, the specific features and steps are disclosed as preferred forms of implementing the claimed invention.

What is claimed is:

1. A method comprising:
    monitoring multiple different variables associated with a patient having congestive heart failure (CHF), the variables comprising time of day, patient activity level, and posture;
    for a given set of variable values, selecting one or more timing parameters that can be used to administer pacing therapy to the patient to improve hemodynamic performance; and
    administering pacing therapy using the selected timing parameters.

2. The method of claim 1, wherein said selecting comprises selecting parameters associated with A-V timing.

3. The method of claim 1, wherein said selecting comprises selecting parameters associated with timing between left and right ventricles (V-V timing).

4. The method of claim 1, wherein said selecting comprises selecting parameters associated with A-V and timing between left and right ventricles (V-V timing).

5. The method of claim 1, wherein said selecting comprises selecting parameters effective to optimize a patient's hemodynamic performance.

6. A stimulation device composing:
    one or more processors;
    memory;
    computer-readable instructions in the memory which, when executed by the one or more processors, cause the processors to:
        monitor multiple different variables associated with a patient having congestive heart failure (CHF), the variables comprising time of day, patient activity level, and posture;
        for a given set of variable values, select one or more timing parameters that can be used to administer pacing therapy to the patient to improve hemodynamic performance; and
        administer pacing therapy using the selected timing parameters.

7. The stimulation device of claim 6, wherein the instructions cause the one or more processors to select parameters associated with A-V timing.

8. The stimulation device of claim 6, wherein the instructions cause the one or more processors to select parameters associated with timing between left and right ventricles (V-V timing).

9. The stimulation device of claim 6, wherein the instructions cause the one or more processors to select parameters associated with A-V timing and timing between left and right ventricles (V-V timing).

10. One or more computer-readable media having instructions thereon which, when executed by an implantable stimulation device, cause the stimulation device to:
    monitor multiple different variables associated with a patient having congestive heart failure (CHF), the variables comprising time of day, patient activity level, and posture;
    for a given set of variable values, select one or more timing parameters that can be used to administer pacing therapy to the patient effective to optimize a patient's hemodynamic performance; and
    administer pacing therapy using the selected timing parameters.

11. The computer-readable media of claim 10, wherein the instructions cause the stimulation device to select parameters associated with A-V timing.

12. The computer-readable media of claim 10 wherein the instructions cause the stimulation device to select parameters associated with timing between left and right ventricles (V-V timing).

13. The computer-readable media of claim 10, wherein the instructions cause the stimulation device to select parameters associated with A-V and V-V timing.

14. A method comprising:
monitoring multiple different variables associated with a patient having congestive heart failure (CHF), the variables being independent of the patient's heart function;
for a given set of variable values, determining whether one or more timing parameters exist that can be used to administer pacing therapy to the patient to optimize the patients hemodynamic performance;
in an event that one or more timing parameters do exist for the given set of variable values, administering pacing therapy to the patent using the existing timing parameters; and
in an event that one or more timing parameters do not exist for the given set of variable values, automatically determining timing parameters that optimize the patient's hemodynamic performance for the given set of variables.

15. The method of claim 14 further comprising administering pacing therapy to the patient using the determined timing parameters.

16. The method of claim 14 further comprising storing the determined timing parameters for future use.

17. The method of claim 14, wherein said automatically determining the timing parameters comprises determining parameters associated with A-V timing.

18. The method of claim 14, wherein said automatically determining the timing parameters comprises determining parameters associated with timing between left and right ventricles (V-V timing).

19. The method of claim 14, wherein said automatically determining the timing parameters comprises determining parameters associated with A-V timing and timing between left and right ventricles (V-V timing).

20. The method of claim 14, wherein one of said variables comprises a time of day variable.

21. The method of claim 14, wherein one of said variables comprises a patient activity level variable.

22. The method of claim 14, wherein one of said variables comprises a patient posture variable.

23. The method of claim 14, wherein said variables comprise one or more of a time of day variable, a patient activity level variable, and a patient posture variable.

24. The method of claim 14, wherein said automatically determining comprises doing so through trial and error techniques.

25. A stimulation device comprising:
one or more processors;
memory;
computer-readable instructions in the memory which, when executed by the one or more processors, cause the processors to:
monitor multiple different variables associated with a patient having congestive heart failure (CHF), the variables being independent of the patient's heart function;
for a given set of variable values, determine whether one or more timing parameters exist that can be used to administer pacing therapy to the patient to optimize the patient's hemodynamic performance;
in an event that one or more timing parameters do exist for the given set of variable values, administer pacing therapy to the patient using the existing timing parameters;
in an event that one or more timing parameters do not exist for the given set of variable values, automatically determine timing parameters that optimize the patient's hemodynamic performance for the given set of variables; and
administer pacing therapy to the patient using the determined timing parameters.

26. The stimulation device of claim 25, wherein the instructions cause the stimulation device to store the determined timing parameters for future use.

27. The stimulation device of claim 25, wherein the instructions cause the stimulation device to automatically determine parameters associated with A-V timing.

28. The stimulation device of claim 25, wherein the instructions cause the stimulation device to automatically determine parameters associated with timing between left and right ventricles (V-V timing).

29. The stimulation device of claim 25, wherein the instructions cause the stimulation device to automatically determine parameters associated with A-V timing and timing between left and right ventricles (V-V timing).

30. The stimulation device of claim 25, wherein one of said variables comprises a time of day variable.

31. The stimulation device of claim 25, wherein one of said variables comprises a patient posture variable.

32. The stimulation device of claim 25, wherein one of said variables comprises a patient activity level variable.

33. The stimulation device of claim 25, wherein said variables comprise one or more of a time of day variable, a patient posture variable, and a patient activity level variable.

34. A method comprising:
monitoring multiple different variables associated with a patient having congestive heart failure (CHF), the variables being independent of the patient's heart function;
for a given set of variable values, determining whether one or more timing parameters exist that can be used to administer pacing therapy to the patient to optimize the patient's hemodynamic performance;
in an event that one or more timing parameters do not exist for the given set of variable values, automatically determining timing parameters that optimize the patient's hemodynamic performance for the given set of variables by using one or more optimization techniques; and
administering pacing therapy using the determined timing parameters.

35. The method of claim 34, wherein said optimization techniques comprise a simplex optimization technique.

36. The method of claim 34, wherein said optimization techniques comprise a steepest descent optimization method.

37. The method of claim 34, wherein said optimization techniques comprise one or more of a simplex optimization technique and a steepest descent optimization method.

38. A method comprising:
defining one or more surfaces that describe optimal timing parameters for pacing a patient with congestive heart failure (CHF), the surfaces being defined as a function of patient posture, time of day, and activity level;
determining a patient's posture, the time of day, and the activity level of the patient;
finding a point on the one or more surfaces that correspond to the patient's posture, the time of day, and the activity level; and
pacing the patient using timing parameters that correspond to said point on the one or more surfaces.

39. The method of claim 38, wherein said timing parameters pertain to A-V timing.

40. The method of claim 38, wherein said timing parameters pertain to timing between left and right ventricles (V-V timing).

41. The method of claim 38, wherein said timing parameters to A-V timing and timing between left and right ventricles (V-V timing).

42. An implantable stimulation device comprising:

one or more processors;

memory;

computer-readable instructions in the memory which, when executed by the one or more processors, cause the processors to:

define one or more surfaces that describe optimal timing parameters for pacing a patient with congestive heart failure (CHF), the surfaces being defined as a function of patient posture, time of day, and activity level;

determine a patient's posture, the time of day, and the activity level of the patient;

find a point on the one or more surfaces that correspond to the patient's posture, the time of day, and the activity level; and pace the patient using timing parameters that correspond to said point on the one or more surfaces.

* * * * *